United States Patent
Pretsch et al.

(10) Patent No.: US 11,013,760 B2
(45) Date of Patent: May 25, 2021

(54) POLYGUANIDINE POLYMERS AND METHODS OF USE THEREOF

(71) Applicant: Sealife Pharma GmbH, Tulln (AT)

(72) Inventors: Alexander Pretsch, Großmugl (AT); Michael Nagl, Vienna (AT); Christoph Wiesner, Vienna (AT); Ralph Hollaus, Vienna (AT); Miroslav Genov, Tulln (AT)

(73) Assignee: SEALIFE PHARMA GMBH, Tulin (AT)

( * ) Notice: Subject to any disclaimer, the term of this patent is extended or adjusted under 35 U.S.C. 154(b) by 0 days.

(21) Appl. No.: 16/411,703

(22) Filed: May 14, 2019

(65) Prior Publication Data

US 2019/0269719 A1    Sep. 5, 2019

Related U.S. Application Data

(62) Division of application No. 15/500,772, filed as application No. PCT/AT2015/050187 on Jul. 30, 2015, now Pat. No. 10,335,431.

(30) Foreign Application Priority Data

Jul. 31, 2014  (AT) .................................. A609/2014

(51) Int. Cl.
| | |
|---|---|
| C07C 279/00 | (2006.01) |
| A61K 31/785 | (2006.01) |
| A61K 45/06 | (2006.01) |
| A61K 31/155 | (2006.01) |
| C07C 277/08 | (2006.01) |
| A01N 47/44 | (2006.01) |
| C07D 213/42 | (2006.01) |
| C08G 73/00 | (2006.01) |
| C08G 73/06 | (2006.01) |

(52) U.S. Cl.
CPC ............ *A61K 31/785* (2013.01); *A01N 47/44* (2013.01); *A61K 31/155* (2013.01); *A61K 45/06* (2013.01); *C07C 277/08* (2013.01); *C07C 279/00* (2013.01); *C07D 213/42* (2013.01); *C08G 73/00* (2013.01); *C08G 73/0627* (2013.01)

(58) Field of Classification Search
None
See application file for complete search history.

(56) References Cited

U.S. PATENT DOCUMENTS

| | | |
|---|---|---|
| 2,325,586 A | 8/1943 | Bolton |
| 2,882,156 A | 4/1959 | Minsk |
| 3,869,478 A | 3/1975 | Bailey |
| 3,901,944 A | 8/1975 | Tomcufcik |

FOREIGN PATENT DOCUMENTS

| | | |
|---|---|---|
| EP | 0619272 A1 | 10/1994 |
| EP | 1172224 A1 | 1/2002 |
| FR | 2827507 A1 | 1/2003 |
| GB | 1095902 A | 12/1967 |
| JP | 2001271293 A | 10/2001 |

OTHER PUBLICATIONS

Saczewski et al. (Expert Opinion on Therapeutic Patents, 2009, 19:10, 1417).*
Wei et al. (e-Polymers, 2012, No. 072, 1-10).*
Wei et al, "Condensation Between Guanidine Hydrochloride and Diamine/Multi-amine and its Influence on the Structures and Antibacterial Activity of Oligoguanidines," e-Polymers, No. 072, pp. 1-10 (2012).

(Continued)

*Primary Examiner* — Sudhakar Katakam
*Assistant Examiner* — Jennifer C Sawyer
(74) *Attorney, Agent, or Firm* — Panitch Schwarze Belisario & Nadel LLP

(57) ABSTRACT

Polyguanidines and methods of use thereof are described. In particular, polyguanidines of formula (I), formula (II), and formula (III) are described. The polyguanidines can be used to treat infection, such as bacterial, viral or fungal infection, and as an ex vivo microbial agent.

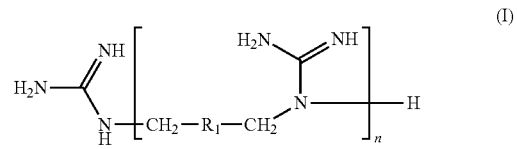

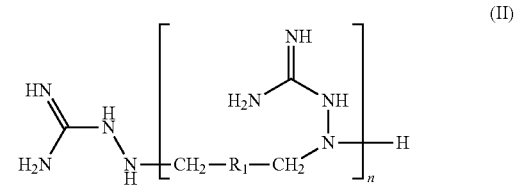

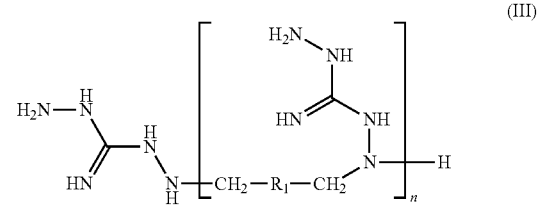

8 Claims, 1 Drawing Sheet

(56) References Cited

OTHER PUBLICATIONS

Gross et al, "Beschleunigung von Substitutionsreaktionen eines Phosphorsiurediesters durch Bis(guanidinium)-Verbindungen," Liebigs Ann Chem., pp. 49-58 (1994).
Battaglia et al, "A Short Synthesis of the Triazolopyrimidine Antibiotic Essramycin," J. Nat. Prod, vol. 73, pp. 1938-1939 (2010).
Int'l Search Report dated Apr. 1, 2016 in Int'l Application No. PCT/AT2015/050187.
Search Report dated Jun. 18, 2015 in AT Application No. A609/2014.
International Preliminary Report on Patentability dated Apr. 1, 2016 in Int'l Application No. PCT/AT2015/050187.

\* cited by examiner

Toxicity Tests – HaCaT Cell Line:
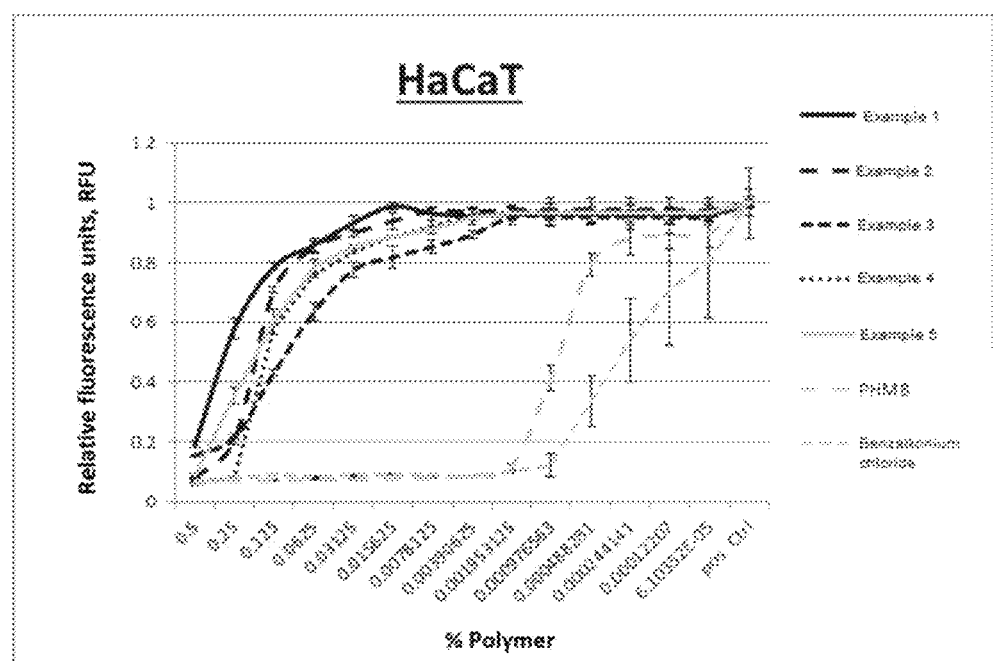

POLYGUANIDINE POLYMERS AND METHODS OF USE THEREOF

CROSS-REFERENCE TO RELATED APPLICATIONS

This application is a Division of co-pending U.S. patent application Ser. No. 15/500,772 filed Jan. 31, 2017, which was a Section 371 of International Application No. PCT/AT2015/050187, filed Jul. 30, 2015, which was published in the German language on Feb. 4, 2016 under International Publication No. WO 2016/015081 A9, which claims priority under 35 U.S.C. § 119(b) to Austrian Application No. A609/2014, filed Jul. 31, 2014, the disclosures of which are incorporated herein by reference in their entirety.

BACKGROUND OF THE INVENTION

The present invention relates to a new method for producing polyguanidines, polycondensation products produced thereby, and their use as antimicrobial or antiinfective agents.

STATE OF THE ART

Polyguanidines of the following formula and various derivatives thereof have been known for a long time.

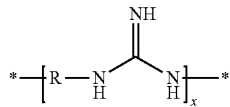

Already in 1943, patent literature described in U.S. Pat. No. 2,325,586 several production methods for various polyguanidines by polycondensation of i) guanidine or salts thereof, ii) cyano halides, iii) dicyanamides, or iv) isocyanide dihalides with diamines, or v) two dicyan-diamides with each other (resulting in cyano-substituted polyguanidines), as well as the use of polyguanidines thus produced as coloring aids:

i)

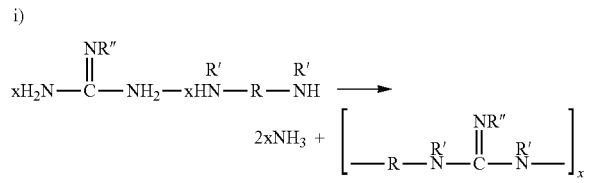

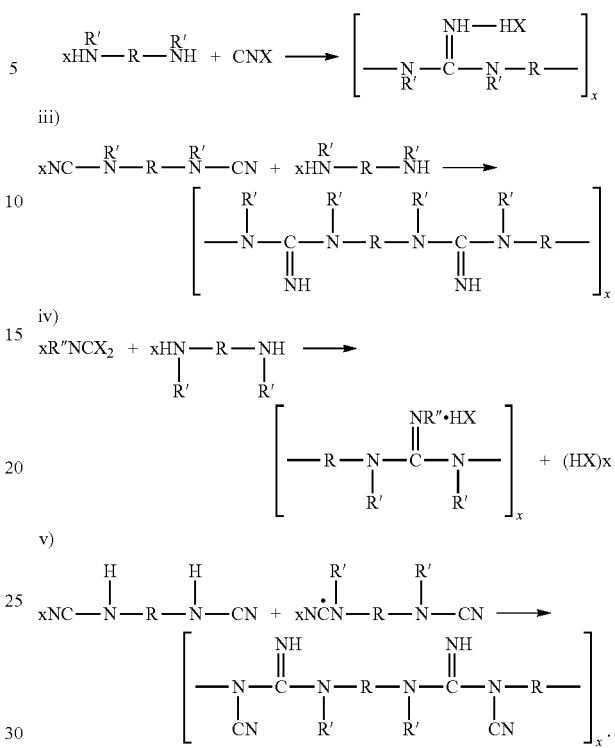

Already at that time, the diamines disclosed for the use in the reactions i) to iv) were alkylene and phenylene diamines as well as oxyalkylene or polyether diamines, later known as Jeffamin®.

Decades later, such polyguanidines have proven to be excellent biocides. A group around Oskar Schmidt disclosed in WO 99/54291 A1 the production of microbiocidal polyhexamethylene guanidines, in WO 01/85676 A1 biocidal polyguanidines produced by condensation of guanidine with polyoxyalkylenes, and in WO 2006/047800 A1 polyguanidine derivatives acting as biocides, particularly fungicides, which are formed by polycondensation of guanidine with a mixture of alkylene diamine and oxyalkylene diamine and allegedly have lower toxicity than polymers containing only one of the two types bivalent residues $R_1$.

WO 02/30877 A1 describes similar polyguanidines as disinfectants, which additionally contain phenylene moieties in the chains. A group of Russian researchers (Tets, Tets, and Krasnov) discloses in WO 2011/043690 A1, from which US 2011/0269936 A1 and EP 2.520.605 A1 were derived, biocidal polyguanidines of the following formula that are produced by polycondensation of guanidine and hexamethylene diamine in the presence of hydrazine hydrate:

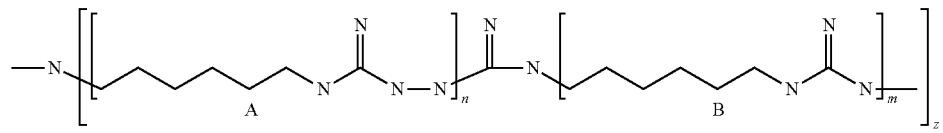

The hydrazine thus replaces during polycondensation—at least formally—an amino group of either only one or two guanidine moieties, which is said to lead to block copolymers wherein poly(hexamethylene guanidine) blocks alternate with poly(hexamethylene aminoguanidine) blocks and wherein the two block types are linked via guanidine dimers, as shown below:

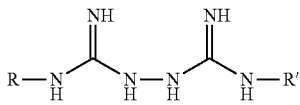

These polymers and acid addition salts thereof also allegedly act as biocides against bacteria, viruses and fungi. However, the examples of these applications, in which 7 different polymers were produced, do not contain any physical data on the products obtained except for the information that the product of Example 1 is a "solid, almost colorless, transparent substance."

Regarding possible structures that may arise during polycondensation of guanidines with diamines, there are several articles by a group of researchers at the Graz University of Technology, e.g. Albert et al., Biomacromolecules 4(6), 1811-1817 (2003), and Feiertag et al., Macromol. Rap. Comm. 24(9), 567-570 (2003). In addition to several possibilities of terminating linear polymer chains with one of the initial monomers, cyclic molecules of the following general formula are usually also formed in a non-negligible portion, which in part depends on the chain length of the diamine:

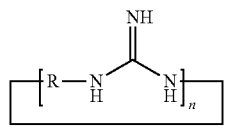

The main disadvantages of practically all of the polyguanidine derivatives described above concern, on the one hand, the non-negligible toxicity of these products and—when highly reactive components are used—their comparatively cumbersome production methods, on the other hand the use of, from a toxicological point of view, problematic components such as hydrazine, which is why the present inventors started researching for solutions.

In the course of their research, the inventors have found out that polycondensation products of amino and diaminoguanidine with amines surprisingly show substantially lower toxicity than the structurally similar polycondensates with guanidine from the documents WO 2011/043690 A1, US 2011/0269936 A1, and EP 2.520.605 A1 cited above, but are also effective antimicrobial substances.

These results are disclosed in the pending patent applications AT A 53/2013 and PCT/AT2014/050026, in which polyguanidine derivatives of the following formula and salts thereof are claimed:

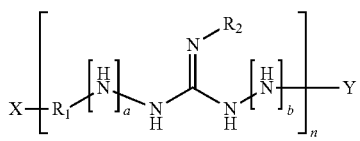

wherein
X is selected from —NH$_2$, aminoguanidino, and 1,3-diaminoguanidino;
Y is selected from —H and —R$_1$—NH$_2$;
or X and Y together form a chemical bond to obtain a cyclic structure;
R$_1$ is selected from divalent organic residues with 2 to 20 carbon atoms, wherein optionally one or more of the carbon atoms are replaced by O or N;
a and b are each 0 or 1, wherein a+b≠2 when no 1,3-diaminoguanidine unites are contained;
R$_2$ is selected from —H and —NH$_2$,
wherein R$_2$ is —NH$_2$ when a+b=0,
R$_2$ is —H or —NH$_2$ when a+b=1, and
R$_2$ is —H when a+b=2; and
n is ≥2.

By analogy with the state of the art known at that time, the method for producing these new poly(di)aminoguanidines consisted in polycondensating corresponding diamines with amino- and/or diaminoguanidines by heating.

Without wishing to be bound by theory, the inventors assume that amino- and diaminoguanidino moieties (in the following collectively referred to as "aminoguanidines," unless the context requires otherwise) are better tolerated by human eukaryotic cells than guanidino moieties and in particular than those polymers containing the hydrazo-bridged guanidine dimers shown above.

However, some of these new aminoguanidine compounds have proven not to be completely satisfactory regarding their antimicrobial effectiveness or toxicity, and the production method is also in need of improvement because the use of certain diamines requires very high temperatures for melt polymerization and it still entails a sometimes problematic residual monomer content.

Thus, the object of the present invention was to provide further polyguanidine derivatives having even better properties as well as an advantageous method for producing the same.

BRIEF DESCRIPTION OF THE DRAWINGS

FIG. 1 shows the proportion of surviving cells of the exposed HaCaT cell line as cell model on the Y axis for polyguanidines according to the present invention.

DISCLOSURE OF THE INVENTION

In a first aspect, the invention achieves this object by providing a method for producing polycondensation products of guanidine, aminoguanidine or diaminoguanidine G with one or more benzyl or allyl derivatives BA according to the following reaction scheme:

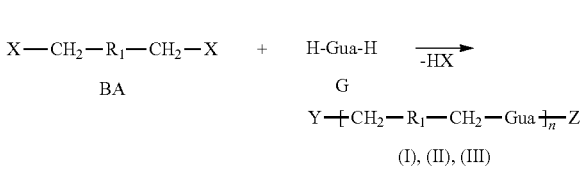

wherein
each X independently represents a leaving group;
each R$_1$ independently represents either an aromatic ring system with at least one aromatic ring, optionally containing one or more hetero atoms selected from O, N and S and optionally being substituted with one or two vinyl groups to which the —CH$_2$—X group(s) is/are bound, or represents ethylene;

Gua represents a guanidindiyl, aminoguanidindiyl or diaminoguanidindiyl residue;

Y represents H-Gua, and

Z represents H; or

Y and Z together represent a chemical bond to obtain a cyclic structure;

wherein at least one benzyl or allyl derivative BA is subjected to a polycondensation reaction with excessive guanidine, aminoguanidine or diaminoguanidine G upon elimination of HX in order to provide a polyguanidine corresponding to the following formula (I), (II) or (III):

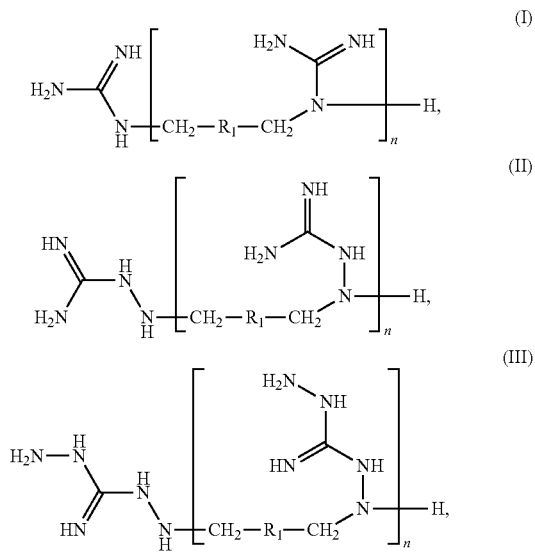

or having a cyclic structure resulting from cyclization upon elimination of a corresponding guanidine, or a salt of said polyguanidine.

Contrary to the state of the art, polycondensation in this production method occurs not by cleaving ammoniak, but by cleaving the leaving group X, preferably in the form of a hydrogen halide, e.g. HCl or HBr, or a sulfonic acid, e.g. CH$_3$SO$_2$OH (MsOH), which forms acid addition salts with the amino or imino groups present in the molecule, which in turn makes the use of an acid scavenger unnecessary.

This also implicates that polycondensation does not necessarily have to be conducted in a molten state, even though, due to procedural economic reasons, melt polymerization is also the preferred reaction route for the present invention. In preferred embodiments, the at least one benzyl or allyl derivate BA is thus reacted with guanidine, aminoguanidine or diaminoguanidine G by heating the reactants to a temperature above their melting points, the polymerization reaction preferably being conducted for a period of at least 2 h, more preferably at least 3 h. In particular, the reaction is—by analogy with an earlier method of the inventors—conducted in two steps at different temperatures, a first lower and a second higher temperature, in order to guarantee a conversion as complete as possible and thus higher chain lengths and at the same time lower residual monomer contents.

Surprisingly, however, the inventors found that the use of benzylic or allylic structures leads to the formation of mixtures of polycondensation products having structures that differ from those known from the state of the art. However, the main products do not correspond to the structures known from earlier applications by the inventors comprising only mono-substituted nitrogen, since such mono-substituted nitrogen appears to preferably react a second time to form the above structures of formulas (I) to (III).

Without wishing to be bound by theory, the inventors assume that the reactivity of the educts, which is due to a mesomeric stabilization of the transition state in the course of the nucleophilic substitution at the benzylic or allylic methylene group, together with the increased reactivity of the primarily formed mono-substituted nitrogen-adducts, leads to the given nitrogen double substitution, which leads to the further assumption that a similar effect is to be expected with at least a majority of known benzylic and allylic structures, i.e. with structures having one methylene group attached to an aromatic ring or a double bond, or with combinations thereof, i.e. in the case of cinnamylic structures in which—regarding the benzyl residue—apparently the known vinylogy effect takes place (see Example 8 below). The latter is, of course, also applicable to conjugated double bonds in aliphatic residues, e.g. in the case of butadiene instead of ethylene. Therefore, any further substituents on these aromatic rings and double bonds shall not be specifically limited at the moment, as long as the aromaticity of the respective ring is not eliminated and the electron density in the aromatic ring or at the double bond is not substantially altered, in particular in the case of tautomeric effects such as keto/enol, imine/ene-amine etc.

In the given structures of formulas (I) to (III), the guanidine or aminoguanidine units are positioned outside of the chain via the nitrogen atom doubly integrated into the chain, which, according to spectroscopic evidence, leads to the structural type of the formulas (I), (II) or (III) in the majority of the oligomer species formed.

The obtained linking type of the new polyguanidines was determined by means of HMBC-NMR: For the polyaminoguanidine of Example 1, for example, the corresponding long range couplings of benzylic CH$_2$ protons bonded via nitrogen (AB system at 3.8 and 4.2 ppm) are detectable by such an N atom integrated into the oligomer chain as well as two benzylic carbon atoms (at 64 ppm). As an indication of higher branched secondary components (~15% according to $^1$H-NMR), signals correlating to benzylation of a further guanidine nitrogen beyond imino functionality were found (AB system at 4.3 and 4.5 ppm, HMBC long range signals in the guanidine carbon region at 160 ppm). A further group of NMR signals CH shift at 8 ppm, $^{13}$C shift at 150 ppm) of benzylic imino functionalities correlates with oligomer counterparts of the Sommelet oxidation type, which corresponds to the mass spectrometric data (doublets of the m/z type [M−2] for all oligomers).

The inventors expected even better antimicrobial activity from this new structural type than from their earlier polyaminoguanidines, which, indeed, was confirmed, as is shown by the exemplary embodiments of the invention below: biocidal activity is clearly increased, while toxicity is even lower at the same time.

Without wishing to be bound by theory, the inventors assume that the latter might result from a higher average chain length compared to earlier polyaminoguanidines as well as from an even lower residual monomer content.

To optimize reaction conditions and to find the best possible compromise between reaction time, chain length and residual monomer content, the inventors conducted test series with varying ratios of benzyl or allyl derivative BA and guanidines G, varying temperatures, as well as varying reaction times, and they found out that a ratio G/BA just below 2 leads to products showing the best biological results, wherein the reaction mixtures should preferably first be heated to a temperature of approximately 150-170° C. for 2 to 3 h and then to a temperature of 180-190° C. for 1 to 2 h.

In a second aspect, the invention provides new polyguanidines corresponding to the following formulas (I) to (III), namely
a polyguanidine corresponding to the following formula (I):

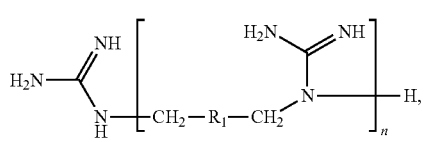

or having a cyclic structure resulting from cyclization upon elimination of a guanidine;
a polyguanidine corresponding to the following formula (II):

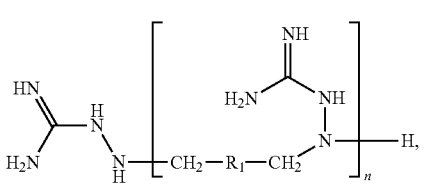

or having a cyclic structure resulting from cyclization upon elimination of an aminoguanidine, and
a polyguanidine corresponding to the following formula (III):

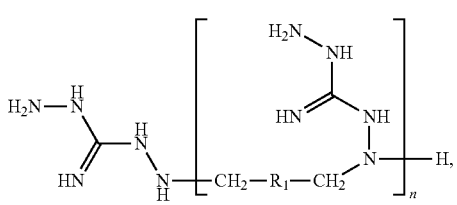

or having a cyclic structure resulting from cyclization upon elimination of a diaminoguanidine;
wherein $R_1$ represents either an aromatic ring system with at least one aromatic ring, optionally containing one or more heteroatoms selected from O, N and S and optionally being substituted with one or two vinyl groups to which the —$CH_2$—X group(s) is/are bound, or represents ethylene, and in preferred embodiments is selected from divalent residues of optionally substituted benzene, divinylbenzene, furan, pyrrole, thiophene, pyridine, biphenyl, fluorene or ethylene, more preferably from a divalent residue of benzene, divinylbenzene, pyridine, biphenyl or ethylene, which residues have already provided good results.

Due to the high antimicrobial effectiveness of the new structures, the invention provides in a third aspect a new polyguanidine as defined above for use as an antibiotic or antiinfective, preferably for antagonizing bacterial, viral or fungal infections in a human or animal patient. The polyguanidine may serve for topical or systemic administration, preferably for administration in the form of a drug or a pharmaceutical composition.

Alternatively, the new polyguanidines may also be used ex vivo as antimicrobial agents, preferably as active components of antimicrobial paints, coatings, foils, or membranes, or the like.

In a fourth aspect, the invention thus provides a drug or a pharmaceutical composition for antagonizing bacterial, viral or fungal infections in a human or animal patient, comprising at least one of the new polyguanidines as an antiinfective and preferably also at least one pharmaceutically acceptable carrier or excipient and optionally one or more adjuvants and/or one or more further active agents.

Preferably, the drug or pharmaceutical composition contains at least one further active agent that also shows an antimicrobial effect in order to increase the effect and utilize possible synergetic effects. The at least one further active agent may also be effective against another conditions than bacterial infections. Examples include antidiarrheals and so-called gastroprotective agents.

Below, the invention will be described in further details by means of non-limiting examples.

EXAMPLES

Example 1

Preparation of Polyaminoguanidine (1)

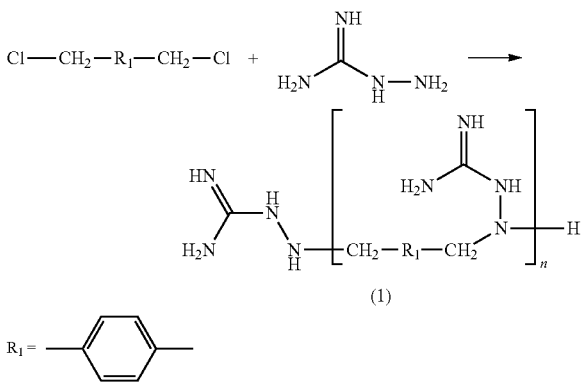

α,α'-Dichloro-p-xylene (880 mg, 5.03 mmol) and 1.95 equivalents of aminoguanidine hydrochloride (1083 mg, 9.80 mmol) were heated with stirring to 160° C. for 3 h in an open reaction vessel, followed by heating to 180° C. for 2 h. After the reaction mixture had cooled to below 80° C., the tenfold amount of water was added to the reaction product, and after thoroughly mixing by means of stirring or ultrasound treatment, a clear, light yellow solution with traces of solid contents was obtained. It was filtered through a 0.2 μm PFTE membrane and then evaporated to obtain polyguanidine (1) as a yellow, amorphous solid.

For analysis, a sample was dissolved in a tenfold amount of $D_2O$. When recording the $^1H$ and the $^{13}C$ NMR spectra, DSS (4,4-dimethyl-4-silapentane-1-sulfonic acid) was added for reference as an internal standard:

$^1H$ NMR ($D_2O$), δ (ppm): 3.72-3.91 (ad, $CH_{2A}$—N(Gua)-$CH_{2A}$, $J_{A,B}$=12.4 Hz, $CH_{2A}$ chain), 3.93-4.05 (as, $CH_2$—NH-Gua, $CH_2$ terminal), 4.10-4.23 (ad, $CH_2B$—N(Gua)-$CH_{2B}$, $J_{A,B}$=12.4 Hz, CH$_2$B chain), 4.29-4.39 (m, CH$_{2A}$ α-Gua), 4.45-4.52 (m, CH$_2$B α-Gua), 7.30-7.83 (m, =CH Ar), 8.08 (as, N=CH).

$^{13}$C NMR (D$_2$O), δ (ppm): 46.25, 46.56, 46.94 (CH$_2$ α-Gua), 56.90, 56.97, 57.03 (CH$_2$ terminal), 63.87, 64.02 (CH$_2$—N(Gua)-CH$_2$ chain), 128.93, 129.04, 129.57, 129.63, 129.78, 129.84, 130.20, 130.32, 130.49, 130.66, 132.10, 132.17, 132.30, 132.40, 132.62, 132.67, 132, 75, 132.83, 132.92, 133.20 (CH Ar), 135.02, 135.19, 137.54, 137.92, 138.13, 138.50, 139.07, 139.23, 141.31, 142.53 (C$_q$ Ar), 150.21, 151.05, 151.12 (N=CH), 157.60, 159.67, 159.73, 160.85 (C$_q$ Gua).

The NMR signals in the ranges of 3.72-3.91 ppm and 4.10-4.23 ppm ($^1$H axis) and at 64.02 ppm ($^{13}$C axis) confirm the presence of a doubly substituted nitrogen atom of the aminoguanidine.

MALDI-MS—MALDI-TOF (in the positive ion mode (matrix suppression off)); scan 20-3000 m/z (deflection off); matrix: ACH (α-cyano-4-hydroxy cinnamic acid); (m/z): 247.3, 249.3, 251.4, 425.3, 427.3, 601.4, 603.4, 777.5, 779.5, 953.7, 955.7, 1129.8, 1131.9, 1306.0, 1308.0, 1482.1, 1484.1, 1658.0, 1660.0, 1834.1, 1836.1, 2010.2, 2012.2, 2186.3, 2188.3, 2362.4.

Example 2

Preparation of Polyaminoguanidine (2)

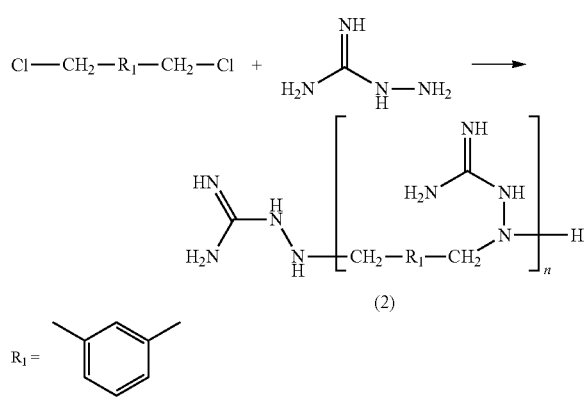

(2)

In analogy to Example 1, polyguanidine (2) was prepared from α,α'-dichloro-m-xylene and aminoguanidine hydrochloride, yielding a yellowish, amorphous, completely water-soluble solid.

$^1$H NMR (D$_2$O), δ (ppm): 3.73-3.92 (ad, CH$_{2A}$—N(Gua)-CH$_{2A}$, $J_{A,B}$=12.7 Hz, CH$_{2A}$ chain), 3.94-4.05 (as, CH$_2$—NH-Gua, CH$_2$ terminal), 4.10-4.23 (ad, CH$_2$B—N(Gua)-CH$_{2B}$, $J_{A,B}$=12.7 Hz, CH$_{2B}$ chain), 4.29-4.38 (m, CH$_{2A}$ α-Gua), 4.45-4.53 (m, CH$_{2B}$ α-Gua), 7.23-7.85 (m, =CH Ar), 8.10 (as, N=CH).

$^{13}$C NMR (D$_2$O), δ (ppm): 46.36, 46.66, 47.01 (CH$_2$ α-Gua), 57.01, 57.04, 57.12, 57.14 (CH$_2$ terminal), 63.94 (CH$_2$—N(Gua)-CH$_2$ chain), 129.63, 129.75, 130.09, 130.20, 130.83, 131.38, 131.44, 131.53, 131.57, 131.67, 131.82, 131.89, 132.18, 132.34, 132.73, 133.52, 134.23, 134.52, 135.29 (CH Ar), 135.72, 135.81, 136.12, 138.59, 138.69, 138.73, 139.13, 139.77, 139.90, 140.30 (C$_q$ Ar), 151.24 (N=CH), 157.67, 159.78, 159.81, 160.86 (C$_q$ Gua).

The NMR signals in the ranges of 3.73-3.92 ppm and 4.10-4.23 ppm ($^1$H axis) and at 63.94 ppm ($^{13}$C axis) again confirm the presence of a doubly substituted nitrogen atom of the aminoguanidine.

MALDI-MS—MALDI-TOF (m/z): 247.3, 249.3, 251.4, 425.3, 427.3, 601.4, 603.4, 777.5, 779.5, 953.7, 955.7, 1129.8, 1131.9, 1306.0, 1308.0, 1482.1, 1484.1, 1658.0, 1660.0, 1834.1, 1836.1, 2010.2, 2012.2, 2186.3, 2188.3.

Example 3

Preparation of Polyaminoguanidine (3)

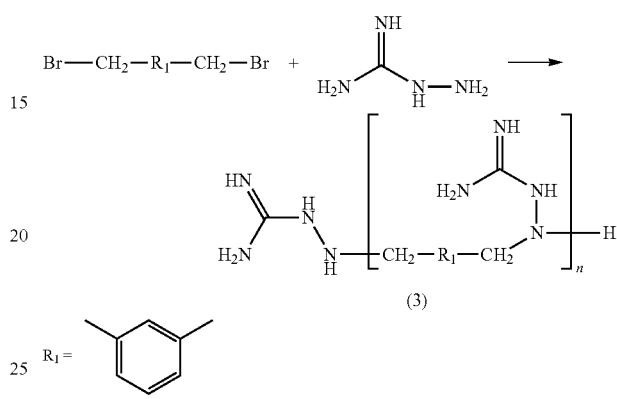

(3)

In analogy to Example 2, polyguanidine (3) was prepared from 132 mg (0.5 mmol) of α,α'-dibromo-m-xylene (instead of the dichloro derivative) as well as 1.75 equivalents of aminoguanidine hydrochloride (97 mg, 0.88 mmol), yielding a brownish, amorphous, water-soluble solid.

$^1$H NMR (D$_2$O), δ (ppm): 3.63-3.95 (m, CH$_{2A}$—N(Gua)-CH$_{2A}$, CH$_{2A}$ chain), 3.95-4.08 (as, CH$_2$—NH-Gua, CH$_2$ terminal), 4.13-4.24 (ad, CH$_{2B}$—N(Gua)-CH$_{2B}$, $J_{A,B}$=12.5 Hz, CH$_2$B chain), 4.31-4.40 (m, CH$_{2A}$ α-Gua), 4.47-4.55 (m, CH$_2$B α-Gua), 7.17-7.86 (m, =CH Ar), 8.12 (as, N=CH).

$^{13}$C NMR (D$_2$O), δ (ppm): 46.38, 46.64, 46.99 (CH$_2$ α-Gua), 56.98, 57.11, 57.48 (CH$_2$ terminal), 63.90 (CH$_2$—N(Gua)-CH$_2$ chain), 128.58, 129.08, 129.64, 129.76, 130.05, 130.20, 130.81, 130.98, 131.35, 131.41, 131.51, 131.71, 131, 80, 131.87, 132.16, 132.33, 132.69, 133.49, 134.21, 134.51, 135.29 (CH Ar), 135.66, 135.76, 136.06, 138.68, 138.98, 139.07, 139.25, 139.72, 139.85, 140.25 (C$_q$ Ar), 150.46, 151.29 (N=CH), 159.73, 160.84 (C$_q$ Gua).

The NMR signals in the ranges of 3.63-3.95 ppm and 4.13-4.24 ppm ($^1$H axis) and at 63.90 ppm ($^{13}$C axis) again confirm the presence of a doubly substituted nitrogen atom of the aminoguanidine.

MALDI-MS—MALDI-TOF (m/z): 247.3, 249.3, 251.4, 425.3, 427.3, 601.4, 603.4, 777.5, 779.5, 953.7, 955.7, 1129.8, 1131.9, 1306.0, 1308.0, 1482.1, 1484.1, 1658.0, 1660.0, 1834.1, 1836.1, 2010.2, 2012.2, 2186.3, 2188.3.

Example 4

Preparation of Polydiamino Guanidine (4)

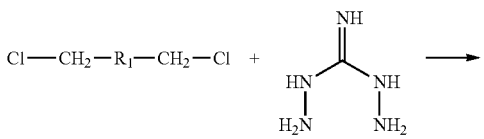

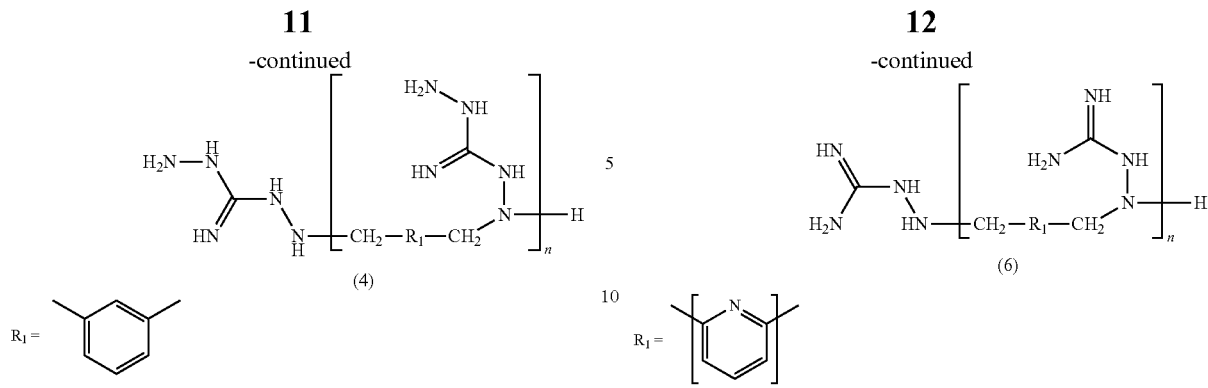

(4)

$R_1 =$

In analogy to Example 2, polyguanidine (4) was prepared from 88 mg (0.5 mmnol) of α,α'-dichloro-m-xylene and 1 equivalent of diaminoguanidine hydrochloride (68 mg, 0.5 mmol), yielding a yellowish, amorphous, water-soluble solid.

The structural determination by means of $^1H$ and $^{13}C$ NMR shows, in addition to the product species found in the Examples 1 to 3, also the presence of larger proportions of highly branched components in which another guanidine nitrogen is benzylized beyond the imino functionality.

Example 5

Preparation of Polyguanidine (5)

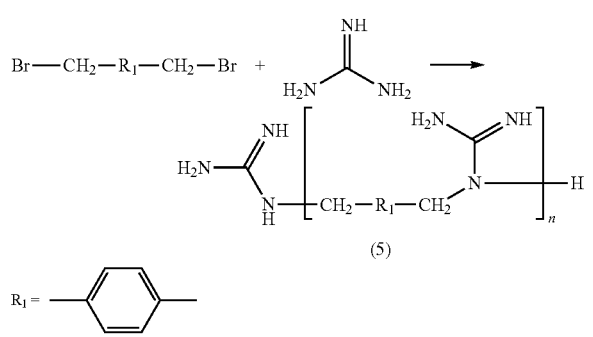

(5)

$R_1 =$

In analogy to Example 3, polyguanidine (5) was prepared from 132 mg (0.5 mmol) of α,α'dibromo-p-xylene and 1.75 equivalents of guanidine hydrochloride (83 mg, 0.88 mmol), yielding a water-soluble, reddish, amorphous solid.

The structural determination by means of and $^{13}C$ NMR shows, in addition to the product species found in the Examples 1 to 3, also the presence of larger proportions of highly branched components in which another guanidine nitrogen is benzylized beyond the imino functionality.

MALDI-MS—MALDI-TOF (m/z): 355.3, 382.3, 516.4, 543.4, 677.3, 704.5, 838.5, 865.5, 999.6, 1026.6, 1160.7, 1187.7, 1321.8, 1348.8, 1483.9, 1510.9, 1672.0, 1833.1, 1995.2.

Example 6

Preparation of Polyaminoguanidine (6)

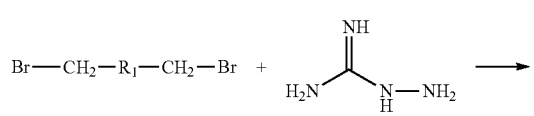

(6)

$R_1 =$ 2,6-Bis(bromomethyl)pyridine (265 mg, 1 mmol) and 1.95 equivalents of aminoguanidine hydrochloride (216 mg, 1.95 mmol) were heated with stirring to 160° C. for 1.5 h in an open reaction vessel, followed by heating to 180° C. for 1.5 h. After the reaction mixture had cooled to below 80° C., water (4.81 ml) was added to the reaction product, and after thoroughly mixing by means of stirring or ultrasound treatment as well as filtration through a 0.2 μm PFTE membrane, a clear, dark brown solution was obtained.

MALDI-MS—MALDI-TOF (m/z): 248.4, 250.4, 252.4, 421.4, 423.4, 425.4, 427.4, 429.4, 598.4, 600.4, 602.4, 604.4.

Example 7

Preparation of Polyaminoguanidine (7)

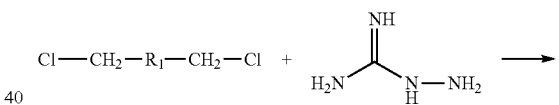

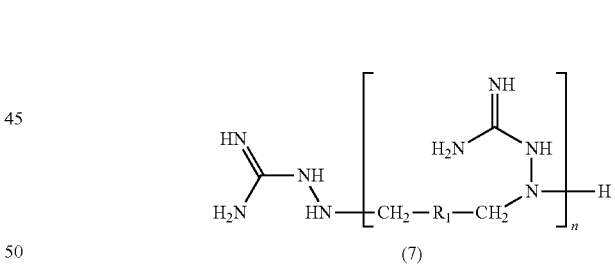

(7)

$R_1 =$

In analogy to Example 2, polyguanidine (7) was prepared from 4,4'-bis(chloromethyl)biphenyl (251 mg, 1 mmol) as well as 1.95 equivalents of aminoguanidine hydrochloride (216 mg, 1.95 mmol), yielding a yellowish, amorphous solid, which is, apart from small amounts of a solid residue, easily soluble in water.

MALDI-MS—MALDI-TOF (m/z): 323.4, 325.4, 327.4, 575.4, 577.4, 579.4, 827.6, 829.6, 831.6.

Example 8

Preparation of Polyaminoguanidine (8)

8.1 Preparation of dimethyl-3,3'-(1,3-phenylene)-(2E,2'E)-diacrylate

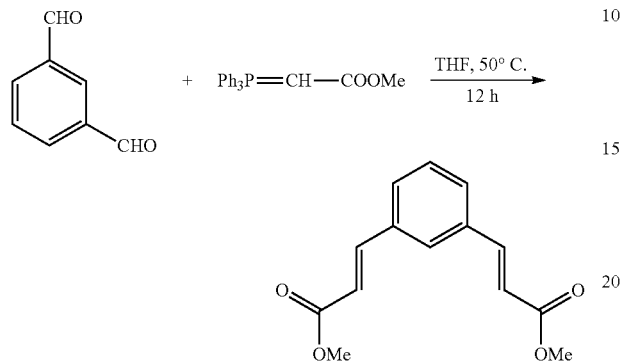

To a solution of 0.75 mmol of isophthalic aldehyde in 10 ml THF, a solution of 2.05 equivalents of (methoxycarbonylmethylene)triphenylphosphorane (1.54 mmol) in 15 ml THF was added with the exclusion of air. The reaction mixture was stirred for 12 h at 50° C. and then concentrated. A chromatographic purification (silica, dichloromethane) yielded 0.62 mmol (83% o.th.) of a white solid.

$^1$H NMR (400 MHz, CDCl$_3$): 3.82 (s, 6H), 6.47 (d, J=16 Hz, 2H), 7.42 (dd, J=7.7+7.7 Hz, 1H), 7.54 (dd, J=7.7+1.7 Hz, 2H), 7.64 (t, J=1.7 Hz, 1H), 7.69 (d, J=16 Hz, 2H).

8.2 Preparation of (2E,2'E)-3,3'-(1,3-phenylene)-bis(prop-2-en-1-ole)

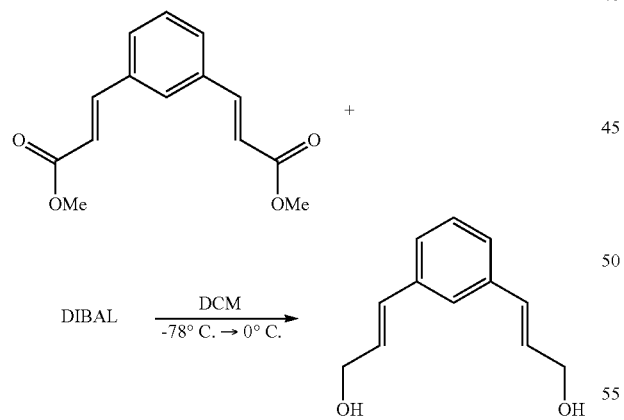

In a Schienk vessel, 1.50 mmol of dimethyl-3,3'-(1,3-phenylene)-(2E,2'E)-diacrylate were dissolved in 30 ml anhydrous dichloromethane. At −78° C., 4.5 equivalents of diisobutyl-aluminum hydride were slowly added dropwise as a 1 M solution in toluene (6.75 ml). The reaction mixture was stirred for 2 h at −78° C. and subsequently hydrolyzed at 0° C. with methanol. The resulting white precipitate was filtered, the filtrate was concentrated and chromatographically purified (silica, DCM:EE 1:1), with 1.05 mmol (70% o.th.) of a white solid being isolated.

$^1$H NMR (400 MHz, CDCl$_3$) δ (ppm): 4.26 (m. 4H), 6.33 (dm. J=16 Hz, 2H), 6.56 (br,d, J=16 Hz, 2H), 7.22 (m, 3H), 7.34 (br s, 1H).

8.3 Preparation of 1,3-bis((E)-3-chloroprop-1-en-1-yl)benzene

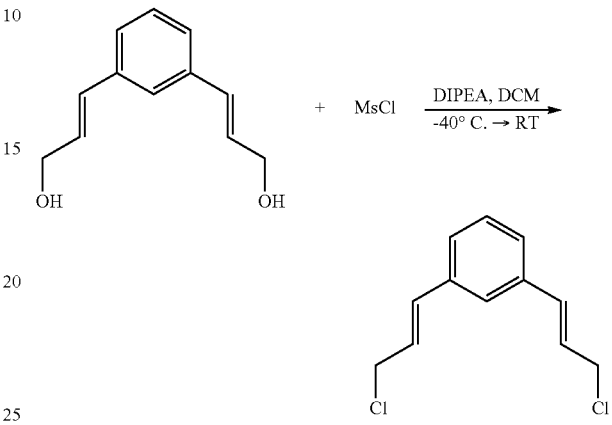

In a Schienk vessel, 0.95 mmol of dimethyl-3,3'-(1,3-phenylene)-(2E,2'E)-diacrylate and 3 equivalents of diisopropylethylamine (DIPEA, 2.85 mmol) in 20 ml dichloromethane were provided and cooled to −40° C., followed by the addition of 2.38 mmol of methanesulfonyl chloride and stirring of the reaction mixture at room temperature for 12 h. After withdrawal of the solvent, the crude product was purified chromatographically (silica, DCM), with 0.57 mmol (60% o.th.) of a white, crystalline solid being isolated.

$^1$H NMR (400 MHz, CDCl$_3$) δ (ppm): 4.25 (dd, J=7.1+1.2 Hz, 4H), 6.34 (dt, J=15.7+7.1 Hz, 2H), 6.65 (dt, J=15.7+1.2 Hz, 2H), 7.30 (m, 3H), 7.40 (m, 1H).

8.4 Preparation of Polyaminoguanidine (8)

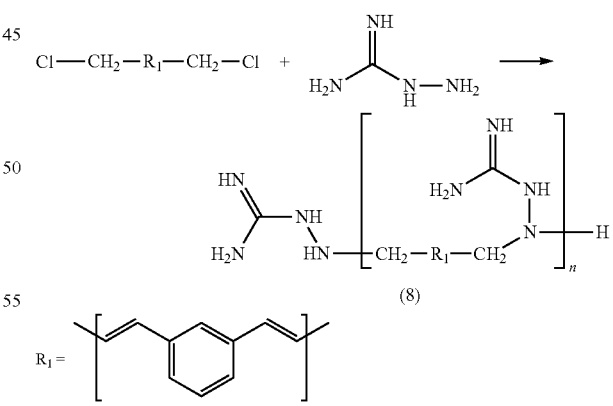

In analogy to Example 2, polyguanidine (8) was prepared from 1,3-bis((E)-2-chlorovinyl)-benzene (200 mg, 1 mmol) and 1.95 equivalents of aminoguanidine hydrochloride (216 mg, 1.95 mmol), yielding a yellowish, translucent, water-soluble gel.

MALDI-MS—MALDI-TOF (m/z): 303.3, 531.4, 759.6, 833.7, 987.8, 1061.9, 1216.0.

Example 9

Preparation of Polyaminoguanidine (9)

9.1 Preparation of cis-1,4-bis(methylsulfonyloxy)but-2-ene

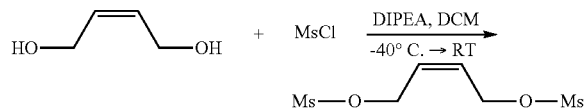

10 g of cis-but-2-ene-1,4-diol (113 mmol) and 3.0 equivalents of diisopropylethylamine (44 g, 340 mmol, 60 ml) were dissolved in 250 ml of dichloromethane and cooled in an argon atmosphere to −40° C., after which 2.4 equivalents of methanesulfonyl chloride (30.9 g, 270 mmol, 20.9 ml) were added portionwise and the reaction mixture was allowed to warm up to +10° C. for 1 h. The clear, yellow solution was poured into 500 ml ice-cold water and the organic phase was washed with further 500 ml of cold water, then with 200 ml of 2 N HCl, then twice with 200 ml each of saturated NaHCO$_3$ solution, and finally again twice with 200 ml each of water. The dichloromethane solution of the product was dried over Na$_2$SO$_4$ and the solvent was withdrawn in vacuo until a white precipitate appeared, whereafter the minimum amount of dichloromethane was added in order to again obtain a clear solution. After the addition of 25 ml of diethylether, the product was left to crystallize from the solution at −20° C., whereafter 10 g of cis-1,4-bis(methylsulfonyloxy)-but-2-ene were isolated as a crystalline, white solid.

$^1$H NMR (400 MHz, CDCl$_3$) δ (ppm): 3.04 (s, 3H), 4.84 (m, 2H), 5.95 (m, 1H).

9.2 Preparation of Polyaminoguanidine (9)

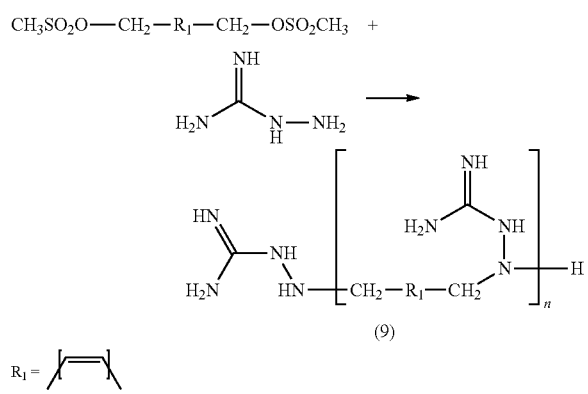

Cis-1,4-bis(methylsulfonyloxy)but-2-ene (246 mg, 1 mmol) and 1.95 equivalents of aminoguanidine hydrochloride (216 mg, 1.95 mmol) were heated in a closed vessel in an argon atmosphere with stirring to 160° C. for 3 h, then to 180° C. for 2 h. After the reaction mixture had cooled to below 80° C., water (4.67 ml) was added to the reaction product to obtain a clear, yellow-red solution.

MALDI-MS—MALDI-TOF (m/z): 201.3, 251.3, 253.3, 297.2, 325.3, 327.3, 349.2, 377.3, 423.3, 451.3, 453.3, 519.3.

Example 10

Preparation of Polyaminoguanidine (10)

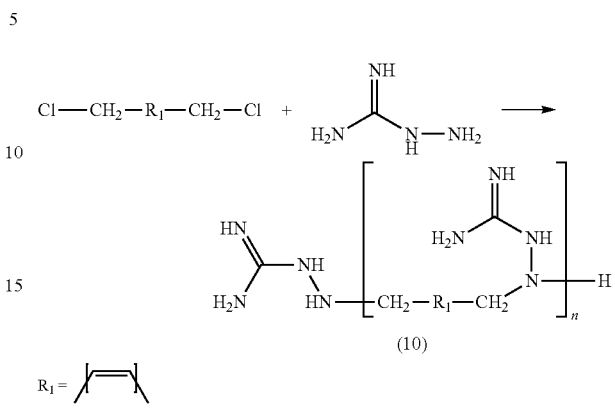

1,4-Dichloro-2-butene (262 mg, 1.3 mmol) and 1.95 equivalents of aminoguanidine hydrochloride (216 mg, 1.95 mmol) were heated in a closed reaction vessel in an argon atmosphere with stirring and repeated (three times per hour) replacement of the atmosphere with fresh argon to 150° C. for 2 h, then to 170° C. for 1 h. After the reaction mixture had cooled to below 80° C., water (4.67 ml) was added to the reaction product to obtain a clear, yellow-red solution.

MALDI-MS—MALDI-TOF (m/z): 201.3, 251.3, 253.3, 297.2, 325.3, 327.3, 377.3, 423.3, 451.3, 453.3.

Comparative Example 1

Preparation of a polyaminoguanidine from diamine and aminoguanidine

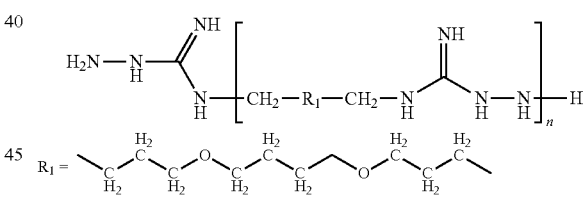

23 mmol of 1,3-diaminoguanidinium hydrochloride and 24 mmol of 4,9-dioxadodecane-1,12-diamine were heated to 120° C. in a reaction vessel closed with a drying tube for 90 min with stirring, whereafter the temperature was increased to 180° C. for 100 min, at the end of which reaction time the pressure was reduced for 45 min (50 mbar). After the reaction mixture had cooled to below 80° C., 25 ml of water were added to the gel-like reaction product. After a few hours, a clear solution was obtained.

The water was evaporated from a sample of the resulting aqueous solution and the obtained residue was dried in vacuum, yielding a reddish, viscous liquid. It was dissolved in 2 ml of D$_2$O (with a deuteration degree >99.5%) and a $^1$H nuclear resonance CH NMR) spectrum was recorded. The position of the groups of methylene protons of the R$_1$ residues thus distinguishable is as follows:

$^1$H NMR (D$_2$O), δ (ppm): 1.54-1.67 (m, OCH$_2$CH$_2$CH$_2$CH$_2$O), 1.80-1.95 (m, NCH$_2$CH$_2$), 3.23-3.38 ppm (m, NCH$_2$), 3.42-3.65 ppm (in, CH$_2$CH$_2$OCH$_2$CH$_2$).

This confirms the structure of the diamine component used, 4,9-dioxadodecan-1,12-diamine.

Example 11

Activity Measurements: Antimicrobial/Antifungal/Antiviral Effect

The activity of the new compounds was tested in screening systems performed several times each. The antibacterial and antifungal activities were examined by means of an MIC test. MIC means "minimal inhibitory concentration" and refers to the lowest concentration of a substance at which no propagation of microorganisms is perceivable with the naked eye. The MIC is determined with a so-called titer process in which the substance is diluted and then the pathogen is added.

This normally serves to determine the concentration of an antibiotic that just inhibits the growth of a bacterial strain. Die MIC is expressed in micrograms per milliliter (μg/ml) or in % by volume, and the dilutions are normally conducted in log 2 steps. Herein, a starting concentration of 1% was diluted twofold each time, leading to test concentrations of 0.5%, 0.25%, 0.125% etc. Lower values thus reflect better activity as antiinfective.

The tests were conducted according to the standards required by EUCAST (European Committee for Antimicrobial Susceptibility Testing) and according to the AFST ("Antifungal Susceptibility Testing") provisions of the European Society of Clinical Microbiology and Infectious Diseases (ESCMID).

The screening system for viruses is an infection system in which host cells are infected in vitro and the test substance is added before or after the infection, followed by the determination of its activity. All these tests were conducted according to internal standard rules of SeaLife Pharma for drug screening using analogous dilution series as in the antibacterial/antifungal test.

In the following Tables 1 to 3, test results regarding the antiinfective effects of the inventive new compounds from the Examples 1, 3, 4 and 5 and from Comparative Example 1 against several multiresistant bacteria and fungi as well as viruses are shown. The data are mean values of multiple determinations.

It is obvious that the new compounds of the invention show excellent activity against gram-positive as well as gram-negative pathogens.

Example 12

Toxicity Tests

Attached FIG. 1 further shows that the inventive new polyguanidines show very low toxicity at those concentrations at which they exhibit excellent antimicrobial activity, as is clearly shown by the proportion of surviving cells of the exposed HaCaT cell line as cell model on the Y axis.

TABLE 1

Effects against gram-positive and gram-negative pathogens

| MIC [%] | MRSA | Enterococcus | Streptococcus pneumoniae | Staphylococcus epidermis | E. coli | Klebsiella pneumoniae | Enterobacter | Pseudomonas aeroginosa | Clostridium def. | Salmonella |
|---|---|---|---|---|---|---|---|---|---|---|
| Example 1 | >0.0016 | >0.0002 | >0.0016 | >0.0008 | >0.0016 | >0.025 | >0.003 | >0.003 | >0.0008 | >0.003 |
| Example 2 | >0.0008 | >0.0008 | >0.0008 | >0.0002 | >0.0008 | >0.025 | >0.0008 | >0.0016 | >0.0004 | >0.0008 |
| Example 3 | >0.0004 | >0.0008 | >0.0008 | >0.0004 | >0.0008 | n.d. | >0.0016 | >0.003 | >0.0004 | >0.0008 |
| Example 4 | >0.003 | >0.003 | >0.003 | >0.0016 | >0.0063 | n.d. | >0.0125 | >0.0125 | >0.003 | >0.0125 |
| Example 5 | >0.0008 | >0.0002 | >0.0004 | >0.0004 | >0.0016 | >0.0125 | >0.0016 | >0.003 | >0.0004 | >0.0016 |
| Example 6 | >0.025 | >0.0125 | >0.025 | >0.025 | >0.025 | >0.05 | >0.025 | >0.025 | >0.025 | >0.05 |
| Example 7 | >0.0002 | >0.0002 | >0.0002 | >0.0002 | >0.0008 | >0.0004 | >0.0008 | >0.0008 | >0.0008 | >0.0008 |
| Example 8 | >0.0004 | >0.0004 | >0.0004 | >0.0004 | >0.0008 | >0.0008 | >0.0008 | >0.0008 | >0.0008 | >0.0008 |
| Example 9 | >0.0125 | >0.003 | >0.0125 | >0.0125 | >0.0008 | >0.0008 | >0.025 | >0.025 | >0.025 | >0.025 |
| Example 10 | >0.0125 | >0.0125 | >0.0125 | >0.0125 | >0.025 | >0.025 | >0.025 | >0.025 | >0.025 | >0.025 |
| Comparative example 1 | >0.001 | >0.008 | >0.004 | >0.001 | >0.016 | >0.02 | >0.008 | >0.02 | n.d. | >0.03 |

TABLE 2

Effects against fungi and yeasts

| MIC [%] | Candida albicans | Candida papillosis | Candida glabrata | Candida krusei | Aspergillus terreus | Aspergilus fumigates | Fusarium rosei | Trichophyton sp. | Alternarria sp. | Microsporum canis | Dematiacea sp. |
|---|---|---|---|---|---|---|---|---|---|---|---|
| Example 1 | >0.025 | >0.025 | >0.025 | >0.025 | >0.05 | >0.05 | >0.05 | >0.025 | >0.025 | >0.025 | >0.025 |
| Example 2 | >0.025 | >0.025 | >0.025 | >0.025 | >0.05 | >0.05 | >0.025 | >0.025 | >0.05 | >0.025 | >0.05 |
| Example 3 | >0.025 | >0.025 | >0.025 | >0.025 | >0.05 | >0.05 | >0.025 | >0.025 | >0.05 | >0.025 | >0.05 |
| Example 4 | >0.05 | >0.05 | >0.05 | >0.05 | >0.1 | >0.1 | >0.1 | >0.05 | >0.05 | >0.05 | >0.1 |
| Example 5 | >0.025 | >0.025 | >0.025 | >0.025 | >0.05 | >0.05 | >0.025 | >0.025 | >0.05 | >0.025 | >0.05 |
| Example 6 | >0.05 | >0.05 | >0.05 | >0.05 | >0.05 | >0.05 | >0.05 | | | | |
| Example 7 | >0.025 | >0.025 | >0.025 | >0.025 | >0.05 | >0.05 | >0.025 | | | | |

TABLE 2-continued

Effects against fungi and yeasts

| MIC [%] | Candida albicans | Candida papillosis | Candida glabrata | Candida krusei | Aspergillus terreus | Aspergilus fumigates | Fusarium rosei | Trichophyton sp. | Alternarria sp. | Microsporum canis | Dematiacea sp. |
|---|---|---|---|---|---|---|---|---|---|---|---|
| Example 8 | >0.025 | >0.025 | >0.025 | >0.025 | >0.05 | >0.05 | >0.05 | | | | |
| Example 9 | >0.05 | >0.05 | >0.05 | >0.05 | >0.05 | >0.05 | >0.05 | | | | |
| Example 10 | >0.05 | >0.05 | >0.05 | >0.05 | >0.05 | >0.05 | >0.05 | | | | |
| Comparative example 1 | >0.008 | >0.03 | >0.02 | >0.02 | >0.02 | >0.03 | >0.03 | >0.02 | >0.02 | >0.03 | >0.02 |

TABLE 3

Effects against viruses

| MIC [%] | Influenza A | Influenza B | Human Rhinovirus |
|---|---|---|---|
| Example 1 | >0.0016 | >0.0016 | >0.0016 |
| Example 2 | >0.0016 | >0.0016 | >0.0016 |
| Example 3 | >0.0016 | >0.0016 | >0.0016 |
| Example 4 | >0.003 | >0.003 | >0.003 |
| Example 5 | >0.0016 | >0.0016 | >0.0016 |
| Example 6 | >0.025 | >0.05 | >0.025 |
| Example 7 | >0.0016 | >0.0016 | >0.0016 |
| Example 8 | >0.0032 | >0.0016 | >0.0032 |
| Example 9 | >0.0125 | >0.0125 | >0.0125 |
| Example 10 | >0.0125 | >0.0125 | >0.0125 |
| Comparative example 1 | >0.035 | >0.008 | >0.008 |

The invention claimed is:

1. A polyguanidine of formula (I), formula (II), or formula (III):

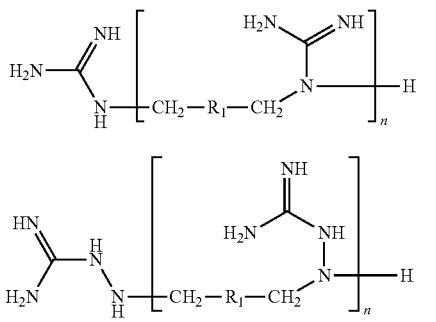

wherein $R_1$ represents either an aromatic ring system with at least one aromatic ring, optionally containing one or more heteroatoms selected from O, N and S and optionally being substituted with one or two vinyl groups to which the —$CH_2$— group(s) is/are bound, or represents ethylene, wherein n is $\geq 2$.

2. The polyguanidine of claim 1, wherein $R_1$ is a divalent residue selected from the group consisting of optionally substituted benzene, divinylbenzene, furan, pyrrole, thiophene, pyridine, biphenyl, fluorene and ethylene.

3. The polyguanidine of claim 2, wherein $R_1$ is a divalent residue selected from the group consisting of benzene, divinylbenzene, pyridine, biphenyl and ethylene.

4. A drug or pharmaceutical composition for antagonizing bacterial infections in a human or animal patient comprising a polyguanidine of claim 1 as an antiinfective.

5. The drug or pharmaceutical composition of claim 4, further comprising at least one pharmaceutically acceptable carrier or excipient and optionally one or more adjuvants and/or one or more further active agents.

6. The drug or pharmaceutical composition of claim 5, comprising at least one further active agent that also shows an antiinfective effect.

7. The drug or pharmaceutical composition of claim 5, comprising at least one further active agent that is effective against a condition other than bacterial infections.

8. The polyguanidine of claim 1, a cyclic structure resulting from cyclization upon elimination of a corresponding guanidine, or a salt of said polyguanidine.

* * * * *